(12) United States Patent
Nishihira et al.

(10) Patent No.: US 6,191,302 B1
(45) Date of Patent: Feb. 20, 2001

(54) PROCESS FOR PRODUCING ALKYL NITRITE

(75) Inventors: Keigo Nishihira; Shuji Tanaka; Shinichi Yoshida, all of Ube (JP)

(73) Assignee: Ube Industries, Ltd., Yamaguchi (JP)

( * ) Notice: Under 35 U.S.C. 154(b), the term of this patent shall be extended for 0 days.

(21) Appl. No.: 09/176,372

(22) Filed: Oct. 21, 1998

(30) Foreign Application Priority Data

Oct. 21, 1997 (JP) .................................................. 9-288278
Nov. 7, 1997 (JP) .................................................. 9-305184

(51) Int. Cl.$^7$ .................................................. C07C 203/02
(52) U.S. Cl. .................................................. 558/488
(58) Field of Search .................................................. 558/488

(56) References Cited

U.S. PATENT DOCUMENTS

| | | | |
|---|---|---|---|
| 4,353,843 | 10/1982 | Doumaux, Jr. et al. | 260/466 |
| 4,461,909 | 7/1984 | Tahara et al. | 560/193 |
| 4,467,109 | 8/1984 | Tahara et al. | 560/193 |
| 4,908,466 | 3/1990 | Nelson | 558/488 |
| 5,214,185 | 5/1993 | Nishihira et al. | 558/277 |
| 5,649,322 | * 7/1997 | Landscheidt et al. | 558/488 |

FOREIGN PATENT DOCUMENTS 0076217   9/1982 (EP) .

* cited by examiner

Primary Examiner—Floyd D. Higel
Assistant Examiner—Ebenezer Sackey
(74) Attorney, Agent, or Firm—Burgess, Ryan & Wayne; Milton J. Wayne; William R. Moran

(57) ABSTRACT

An alkyl nitrite can be produced on an industrial scale with a high efficiency and with a low yield of by-products by the process wherein nitrogen oxide-containing feed gas is brought into an alkyl alcohol liquid in a distillation column reactor while circulating a liquid fraction, produced in the reactor and containing the alkyl alcohol, through a circulation path including a lower section of the reactor and a cooler to remove the reaction heat vigorously generated in the reactor, and while controlling the weight ratio of the circulating liquid fraction to the total alkyl alcohol fed into the reactor to 50:1 to 200:1, the molar ratio of the total alkyl alcohol fed to the reactor and contained in the circulating liquid fraction to nitrogen oxide in the feed gas to 20:1 to 150:1, and the content of the alkyl alcohol in the liquid fraction to 15 to 60% by weight; and the resultant gas fraction containing the target alkyl nitrite is collected from the reactor.

9 Claims, 2 Drawing Sheets

PROCESS FOR PRODUCING ALKYL NITRITE

BACKGROUND OF THE INVENTION

1. Field of the Invention

The present invention relates to a process for producing an alkyl nitrite. More particularly, the present invention relates to a process for producing an alkyl nitrite by reaction of nitrogen oxide with an alkyl alcohol with high efficiency and high industrial stability, while effectively removing the resultant heat generated by the reaction.

The alkyl nitrite produced by the process of the present invention is useful for the production of a dialkyl oxalate by reaction of the alkyl nitrite with carbon monoxide or production of a dialkyl carbonate from the alkyl nitrite by a non-phosgene method.

2. Description of the Related Art

As methods for producing nitrite esters, Japanese Examined Patent Publication No. 61-6,057 and No. 61-26,977 disclose preparation of methyl nitrite by reacting an alcohol with nitrogen oxide in the gas phase in a production process of dimethyl oxalate, and Japanese Examined Patent Publication No. 62-47,867 and No. 63-35,617 and Japanese Unexamined Patent Publication No. 6-25,104 disclose preparation of nitrite esters by reaction of alcohols with nitrogen oxide in a gas phase.

In the reaction of a lower alkyl alcohol, for example, methyl alcohol, with a nitrogen oxide gas containing, as a principal component, nitrogen monoxide, however, a large amount of heat of reaction is generated in accordance with the following reaction:

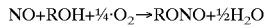

$$NO + ROH + \tfrac{1}{4} O_2 \rightarrow RONO + \tfrac{1}{2} H_2O$$

Accordingly, to prepare the nitrite ester in a high yield at a high degree of safety, it is important that the reaction temperature be closely controlled within an appropriate temperature range, and a reckless run of the reaction due to the reaction heat be prevented. However, the above-mentioned prior publications are completely silent as to concrete means for removing the reaction heat and for appropriately controlling the reaction temperature, and therefore the industrial production of nitrite esters by the above-mentioned prior art was very difficult.

In Japanese Unexamined Patent Publication No. 6-298,706, it is described that the reaction heat can be removed and the reaction temperature can be controlled by injecting an alcohol liquid into a reaction region in which the nitrite ester is produced, to remove the reaction heat by a latent evaporation heat of the alcohol.

In the removal method of reaction heat in accordance with Japanese Unexamined Patent Publication No. 6-298,706, however, the reaction temperature may not always be controlled in the production of the nitrite ester, or the above-mentioned reaction may not be appropriately and fully maintained. Therefore, the production of the nitrite ester was very difficult to effect on an industrial scale and with a satisfactory reproducibility. Japanese Unexamined Patent Publication No. 1-121,251 discloses a process for producing an alkyl nitrite, and a reaction vessel for the process. In this process, a nitrite ester (an alkyl nitrite) is produced by reacting nitrogen oxide with a lower alcohol and oxygen in a reaction region including at least two sections, namely a reaction section in which a gas/liquid contact procedure and a cooling procedure are carried out, and a refining section in which a vapor-residing time long enough to enhance the conversion of oxygen be obtained and a refining capacity large enough to reduce the contents of water and nitric acid in the reaction gas.

Further, Japanese Unexamined Patent Publication No. 1-121,251 discloses concrete means for removing heat from the reaction vessel, namely, a means for withdrawing a liquid side flow from a lower packing section, a means for cooling the liquid side flow, and a means for returning the liquid side flow into the reaction vessel.

The process and apparatus of Japanese Unexamined Patent Publication No. 1-121,251 is disadvantageous in that even when the above-mentioned cooling means is used and the reaction of nitrogen oxide with an alcohol is carried out, although the removal of the reaction heat can be effected with a certain extent, the nitrite ester cannot be obtained in a high yield with a satisfactory degree of stability, and/or by-products, for example, nitric acid, are produced in a large amount, and thus the above-mentioned reaction cannot be stably carried out with a high efficiency.

SUMMARY OF THE INVENTION

An object of the present invention is to provide a process for producing an alkyl nitrite by reacting an alkyl alcohol with nitrogen oxide gas containing nitrogen monoxide, in which process, the alkyl nitrite-producing reaction can be maintained at an appropriate condition, and the reaction temperature can be controlled to an appropriate level by removing the reaction heat with a high efficiency, and thus various problems which occur in conventional process can be prevented.

The above-mentioned object can be attained by the process of the present invention for producing an alkyl nitrite. The process of the present invention comprises the steps of:

(1) feeding an alkyl alcohol liquid into an upper section of a distillation column reactor in which the upper section is connected to a lower section having a bottom portion in which a liquid bottom fraction containing the alkyl alcohol is accumulated, while allowing the alkyl alcohol liquid feed to flow downward through the upper and lower sections;

(2) circulating the alkyl alcohol-containing liquid fraction through a circulating path through which the liquid bottom fraction is withdrawn from the bottom portion of the lower section of the distillation column reactor, the withdrawn liquid fraction is cooled, and then the cooled liquid fraction is returned into an upper portion of the lower section of the distillation column reactor, thereby to cause the returned liquid fraction to flow downward through the lower section of the distillation column reactor;

(3) introducing a feed gas containing nitrogen oxide into the lower section of the distillation column reactor, while allowing the fed feed gas to flow upward through the lower section of the distillation column reactor, and to come into countercurrent contact with the alkyl alcohol liquid and the alkyl alcohol-containing liquid fraction flowing downward through the lower section, whereby a gas-liquid reaction of the nitrogen oxide in the feed gas with the alkyl alcohol is effected in the lower section to produce an alkyl nitrite; and (4) delivering a resultant gas fraction containing the alkyl nitrite from the distillation column reactor, wherein
  (a) the total amount of the liquid fraction circulating through the lower section of the distillation column reactor is controlled to a level of 50 to 200 times the total amount of the alkyl alcohol fed into the distillation column reactor;

(b) the total molar amount of the alkyl alcohol fed into the distillation column reactor and the alkyl alcohol contained in the liquid fraction circulating through the lower section of the distillation column reactor is controlled in a molar ratio of 20:1 to 150:1 to the molar amount of nitrogen oxide contained in the feed gas fed into the lower section of the distillation column reactor; and (c) the content of the alkyl alcohol in the liquid bottom fraction accumulated in the bottom portion of the distillation column reactor is maintained at a level of 15 to 60% by weight.

In the process of the present invention, the feed gas for the distillation column reactor may be supplied from a process for producing an alkyl oxalate in which carbon monoxide and an alkyl nitrite are reacted in the presence of a catalyst in a reactor to produce a gas fraction containing a dialkyl oxalate; the resultant gas fraction is fed into an absorption column in which the gas fraction is brought into contact with an absorption liquid comprising an alkyl alcohol, to produce a condensed liquid fraction containing the dialkyl oxalate absorbed in the alkyl alcohol-containing absorption liquid and a non-condensed gas fraction containing a vapor of the alkyl alcohol and gaseous nitrogen monoxide; and the non-condensed gas fraction is delivered from the absorption column and fed, as a feed gas, into the distillation column reactor to produce the gas fraction containing the alkyl nitrite.

DESCRIPTION OF THE PREFERRED EMBODIMENTS

Figure 1:
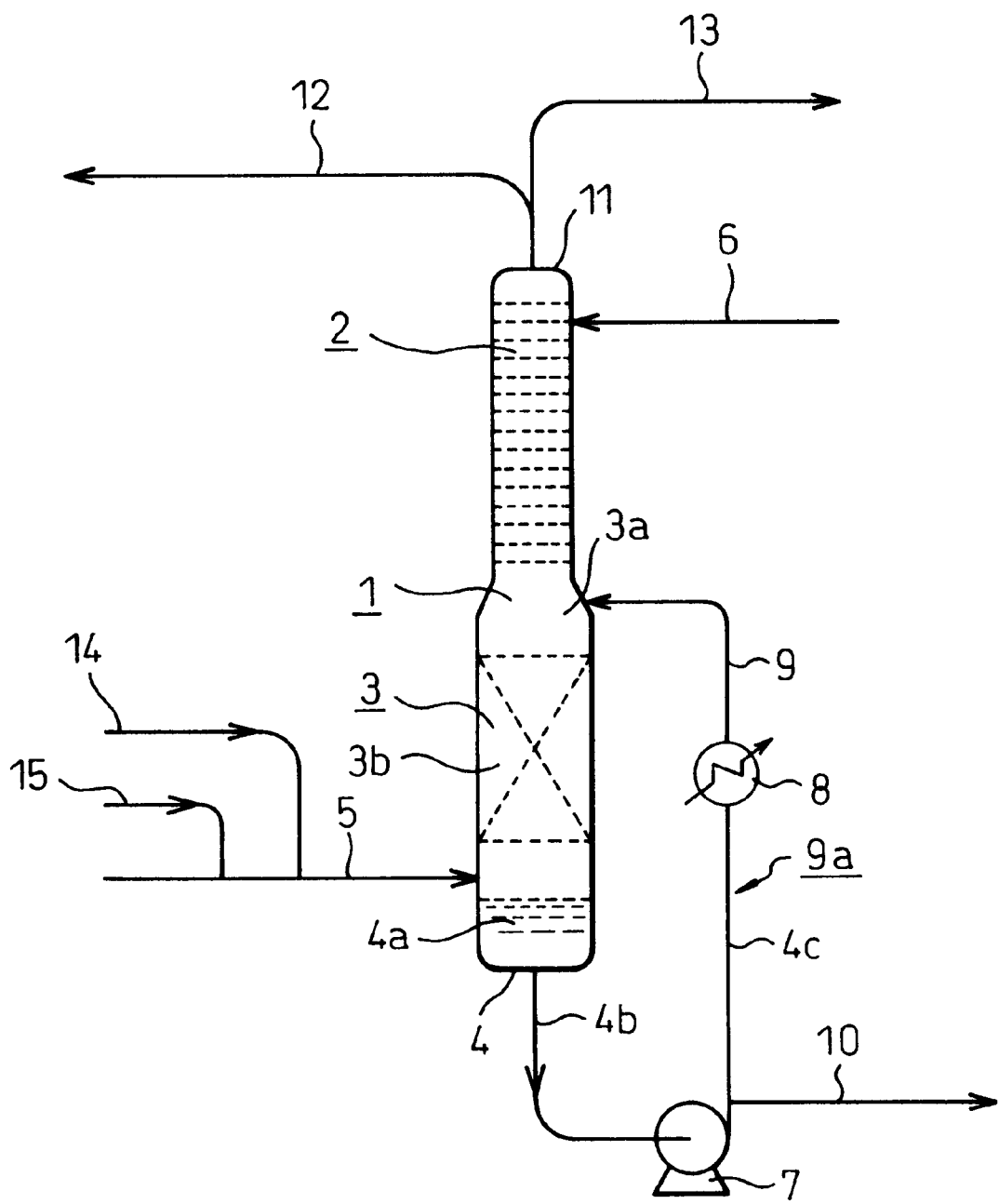
FIG. 1 is an explanatory diagram showing an embodiment of the process of the present invention for producing an alkyl nitrite.

The present invention provides a process for industrially producing an alkyl nitrite by a gas/liquid countercurrent contact reaction of an alkyl alcohol liquid with a nitrogen oxide-containing gas, in which process, the alkyl alcohol liquid is fed into an upper section of a distillation column reactor and flows downward through the reactor from the upper section to a lower section thereof, and a feed gas containing nitrogen oxide is fed into a bottom portion of the reactor (namely a reactor portion below the portion through which the liquid fraction withdrawn from the reactor flows downward), and flows upward through the reactor to cause the upward flow of the feed gas to come into countercurrent contact with the downward flow of the alkyl alcohol liquid. The process of the present invention is useful for the production of the alkyl nitrite in a large amount.

Namely, in the process of the present invention, (1) an alkyl alcohol liquid is fed into an upper section of a distillation column reactor in which the upper section is connected to a lower section having a bottom portion in which a liquid bottom fraction containing the alkyl alcohol is accumulated, while allowing the fed alkyl alcohol liquid to flow downward through the upper and lower sections;

(2) the alkyl alcohol-containing liquid fraction is circulated through a circulating path through which the liquid bottom fraction is withdrawn from the bottom portion of the lower section of the distillation column reactor, the withdrawn liquid fraction is cooled, and then the cooled liquid fraction is returned into an upper portion of the lower section of the distillation column reactor, thereby to cause the returned liquid fraction to flow downward through the lower section of the distillation column reactor;

(3) a feed gas containing nitrogen oxide is introduced into the lower section of the distillation column reactor, while allowing the fed feed gas to flow upward through the lower section of the distillation column reactor, and to come into countercurrent contact with the alkyl alcohol liquid and the alkyl alcohol- containing liquid fraction flowing downward through the lower section, whereby a gas-liquid reaction of the nitrogen oxide in the feed gas with the alkyl alcohol is effected in the lower section to produce an alkyl nitrite; and (4) a resultant gas fraction containing the alkyl nitrite is delivered from the distillation column reactor.

In the process of the present invention, the circulation of the liquid fraction is carried out under the following conditions (a), (b) and (c);

(a) the total amount of the liquid fraction circulating through the lower section of the distillation column reactor is controlled to a level of 50 to 200 times the total amount of the alkyl alcohol fed into the distillation column reactor;

(b) the total molar amount of the alkyl alcohol fed into the distillation column reactor and the alkyl alcohol contained in the liquid fraction circulating through the lower section of the distillation column reactor is controlled in a molar ratio of 20:1 to 150:1 to the molar amount of nitrogen oxide contained in the feed gas fed into the lower section of the distillation column reactor; and (c) the content of the alkyl alcohol in the liquid bottom fraction accumulated in the bottom portion of the distillation column reactor is maintained at a level of 15 to 60% by weight.

In the process of the present invention, the gas/liquid contact reaction is most vigorously effected in the lower section of the distillation column reactor in which the feed gas is fed, and therefore, it is necessary that the reaction heat generated in the lower section of the reactor is removed with a high efficiency, to stabilize the reaction in an appropriate condition and to prevent irregular side reactions.

For this purpose, in the process of the present invention, the liquid bottom fraction accumulated in the bottom portion of the reactor and comprising an aqueous solution of the alkyl alcohol in a content of about 15 to 60% by weight is withdrawn from the bottom portion of the reactor and cooled, by a cooler, the cooled liquid fraction is returned into a portion located above the lower section of the reactor and then flows downward through the lower section of the reactor. When the cooling and circulation of the liquid fraction are carried out under the above-mentioned conditions (a), (b) and (c), the process of the present invention is advantageous in that the reaction heat generated mainly in the lower section of the reactor can be certainly removed with a high efficiency, and the gas/liquid contact reaction for the production of the alkyl nitrite can be effected at appropriate condition in the reaction system, and simultaneously the production of nitric acid, as a by-product can be restricted to a low level.

The process of the present invention will be explained with reference to the attached drawings.

FIG. 1 is an explanatory diagram illustrating a process of the present invention in which a nitrogen oxide-containing feed gas is brought into contact with an alkyl alcohol-containing liquid in a countercurrent relation to each other to effect a gas/liquid contact reaction for producing an alkyl nitrite.

Referring to FIG. 1, an alkyl alcohol liquid is fed into an upper section 2 of a distillation column reactor 1 through an alcohol liquid-feeding conduit 6, while allowing the fed alkyl alcohol liquid to flow downward through the reactor 1 from the upper section 2 to a lower section 3 of the reactor 1. Also, an alkyl alcohol-containing liquid bottom fraction 4a accumulated in a bottom portion 4 of the lower section 3 of the reactor 1 is withdrawn from the bottom portion 4 through a conduit 4b by means of a liquid-transporting means, for example, a pump 7, and then through a conduit 4c, and cooled by a cooler 8 to a desired temperature. The cooled liquid fraction 4a is returned into a portion 3a located above and close to the lower section 3 of the reactor 1 through a conduit 9. The returned liquid fraction 4a flows downward through the lower section 3 of the reactor from the portion 3a to the bottom portion 4.

Namely, the liquid bottom fraction 4a is circulated through a circulating path formed by the lower section 3 (including the returning portion 3a and the bottom portion 4, the conduit 4b, the pump 7, the conduit 4c, the cooler 8 and the conduit 9).

A nitrogen oxide-containing feed gas is fed into the lower section 3 of the reactor 1 through a gas-feeding conduit 5, and is allowed to flow upward through the lower section of the reactor 1 and to come into contact with the liquid fraction flowing downward through the lower section 3 of the reactor 1 in a countercurrent relation to each other. The countercurrent-contacted nitrogen oxide and alkyl alcohol are reacted with each other by a gas/liquid contact reaction to produce a target alkyl nitrite.

In the circulating path of the liquid fraction, a portion of the withdrawn liquid fraction is optionally discharged, before the cooling, through a discharge conduit 10.

A resultant alkyl nitrite-containing gas fraction flows upward through the upper section 2 of the reactor 1 and is delivered through a top portion 11 of the reactor 1 and a delivering conduit 12. Optionally, a portion of the delivered alkyl nitrite-containing gas fraction is discharged (purged) through a discharge conduit 13.

The nitrogen oxide-containing feed gas may contain molecular oxygen supplied through a conduit 14. When the feed gas is supplied from a dialkyl oxalate production process, the feed gas may be added with additional nitrogen oxide gas comprising nitrogen monoxide, nitrogen dioxide and/or nitrous acid supplied through a conduit 15.

In the production of the alkyl nitrite in accordance with the process of the present invention, the following conditions are necessary.

(a) The total amount of the alkyl alcohol-containing liquid fraction circulating through the lower section of the distillation column reactor is controlled to 50 to 200 times, preferably 60 to 180 times, more preferably 70 to 160 times, the total amount of the alkyl alcohol fed into the distillation column reactor.

(b) Also, the total molar amount of the alkyl alcohol fed into the distillation column reactor and the alkyl alcohol contained in the liquid fraction circulating through the lower section of the distillation column reactor is controlled in a molar ratio thereof to the molar amount of nitrogen oxide contained in the feed gas fed into the lower section of the distillation column reactor, of 20:1 to 150:1, preferably 30:1 to 120:1.

(c) Further, the content of the alkyl alcohol contained in the liquid bottom fraction accumulated in the bottom portion of the distillation column reactor is maintained at a level of 15 to 60% by weight, preferably 20 to 55% by weight.

When the circulating amount of the liquid fraction is too small, the removal of the reaction heat generated by the gas/liquid contact reaction carried out in the lower section of the distillation column reactor cannot be evenly and sufficiently carried out; or packing material packed in the lower section of the reactor cannot be maintained in an evenly wetted condition with the alkyl alcohol in the state of a liquid and present in the lower section of the reactor, and thus is in very unevenly wetted condition; thus the gas/liquid contact reaction of the nitrogen oxide-containing feed gas with the alkyl alcohol liquid in the reactor cannot be evenly carried out in a stabilized condition. Also, when the circulating amount of the liquid fraction is too large, a large amount of energy is necessary for the cooling and circulating procedures and thus an economical disadvantage occurs.

Preferably, the cooling and circulation of the alkyl alcohol-containing liquid fraction in the distillation column reactor are forcibly carried out by withdrawing a portion of the liquid bottom fraction 4a from the bottom portion 4 through a conduit 4b by a liquid-transporting means, for example, a pump 7; feeding the withdrawn liquid fraction 4a into a cooler 8 through a conduit 4c; and cooling the liquid fraction by the cooler 8 to a desired temperature of 3 to 20° C., more preferably 5 to 10° C. below the temperature of the liquid bottom fraction accumulated in the bottom portion 4 of the reactor 1, and within the range of OC to 50° C.

In the process of present invention, as shown in FIG. 1, a minor portion of the withdrawn liquid fraction from the bottom portion 4 of the distillation column reactor is optionally discharged to the outside of the reaction system for the process of the present invention, through a conduit 10, after passing through the pump 7 and before reaching the cooler 8, through a discharge conduit 10, and the remaining major portion of the liquid fraction is fed into a cooler 8 to cool to a desired temperature and is returned into a portion 3a immediately above the lower section 3 of the reactor 1, to forcibly circulate the liquid fraction.

When the molar ratio of the total molar amount of the alkyl alcohol fed into the distillation column reactor and the alkyl alcohol contained in the liquid fraction circulating through the lower section of the reactor to the molar amount of nitrogen oxide contained in the feed gas fed into the lower section of the reactor is less than 20:1, the gas/liquid contact reaction of the nitrogen oxide gas with the alkyl alcohol liquid in the lower section of the distillation column reactor cannot be uniformly carried out with a high efficiency, or the reaction occurs locally and thus the reaction temperature cannot be controlled with a high degree of stability. Also, when the molar ratio is more than 150:1, the amount of non-reacted alkyl alcohol which should be recovered and recycled to the process of the present invention becomes too large and thus an economical disadvantage occurs.

When the content of the alkyl alcohol in the liquid bottom fraction accumulated in the bottom portion of the distillation column reactor is lower than 15% by weight, undesirable side reactions occur during the gas/liquid contact reaction and thus by-products such as nitric acid are produced in a large amount. Also, if the alkyl alcohol content in the liquid bottom fraction is more than 60% by weight, undesirable side reactions easily occur.

The alkyl alcohol for the process of the present invention is determined in response to the type of the target alkyl nitrite. For example, lower alkyl alcohols having 1 to 8 carbon atoms, preferably 1 to 6 carbon atoms, more preferably 1 to 2 carbon atoms for example, methyl alcohol and ethyl alcohol are usable for the process of the present invention.

In the process of the present invention, the alkyl alcohol liquid is preferably cooled to a temperature of −15° C. to 30° C., more preferably −10° C. to 20° C. and then fed into a top portion 11 of the upper section 2 of the distillation column reactor 1 to cause the fed alkyl alcohol liquid to flow downward through the upper section 2 and then through the lower portion 3. The feeding of the alkyl alcohol liquid into the top portion of the reactor is preferably effected in an amount of the alkyl alcohol of 0.2 to 3 moles, more preferably 0.3 to 2 moles per mole of the nitrogen oxide in the feed gas fed into the lower section of the reactor.

In the process of the present invention, the alkyl alcohol may be fed in the state of a vapor or a liquid into the lower section of the reactor, together with the nitrogen oxide-containing feed gas or through a feeding conduit different from the feed gas-feeding conduit.

In the process of the present invention, the total feeding amount of the alkyl alcohol is a sum of all the amounts of the alkyl alcohol fed in the state of a vapor and of a liquid from the outside of the reactor into the reactor. For example, referring to FIG. 1, the total feeding amount of the alkyl alcohol is the sum of the amount of the alkyl alcohol contained in the alkyl alcohol liquid fed into the top portion 11 of the reactor 1 through the conduit 6, and the amount of the alkyl alcohol fed in the state of a vapor, together with the feed gas, into the lower section 2 of the reactor through the conduit 5. The total feeding amount of the alkyl alcohol does not contain the amount of the alkyl alcohol contained in the circulating liquid fraction and returned into the lower section of the reactor.

The total feeding alcohol of the alkyl amount is preferably 0.5 to 6 moles, more preferably 1 to 5 moles per mole of the nitrogen oxides contained in the feed gas.

In the process of the present invention, the feed gas preferably contains nitrogen oxide including nitrogen monoxide, nitrogen dioxide and dinitrogen trioxide, in a content of about 3 to 40% by volume, more preferably 5 to 20% by volume, and the nitrogen oxide preferably contain nitrogen monoxide in a content of 50 molar % or more, more preferably 60 to 100 molar %, based on the total amount of the nitrogen oxide. Also, the feed gas preferably contains molecular oxygen in an amount of 0.02 to 0.25 mole per mole of the nitrogen oxide.

The feed gas is optionally diluted by an inert gas consisting of at least one member selected from, for example, nitrogen and carbon dioxide gases. In this case, the amount of the inert gas is preferably 10 to 90%, more preferably 20 to 80% by volume, based on the volume of the feed gas. Further, the feed gas is optionally accompanied by a vapor of an alkyl alcohol in an amount of 2 to 40% by volume based on the volume of the feed gas.

In the process of the present invention, the gas/liquid contact reaction of the nitrogen oxide with the alkyl alcohol is preferably carried out at a temperature of 0 to 100° C., more preferably 5 to 80° C., still more preferably 10 to 60° C., while maintaining the reaction temperature as constant as possible.

The distillation column reactor usable for the process of the present invention is not limited to specific type of reactor as long as the reactor has an upper section 2 in which the resultant gas fraction is fractionated by absorbing and removing water produced as a by-product in the reactor 1 and contained in the reaction product gas, and a lower section 3 in which the gas/liquid contact reaction of the nitrogen oxide in the feed gas with the alkyl alcohol in the liquid state is mainly carried out.

The upper section 2 of the distillation column reactor 1 is not limited to a specific style of section, as long as the alkyl alcohol liquid can flow downwardly through the upper section, and the flowing alkyl alcohol liquid can be fractionated in the upper section, and may be selected from those of a multi-tray distillation column type having a plurality of distillation trays, for example, sieve trays or valve trays, or a packed column type in which a packing material, for example, Raschig rings or poll rings are packed. In the process of the present invention, the multi-tray distillation column type upper section is preferred.

The lower section 3 of the distillation column reactor 1 is not limited to a specific type of section, as long as the gas/liquid contact reaction of the nitrogen oxide gas with the alkyl alcohol liquid can be carried out with a satisfactory efficiency. For example, the lower section 3 may be selected from the multi-tray distillation column type sections and the packed column type sections, as mentioned above for the upper section.

The distillation column reactor 1 usable for the process of the present invention as shown in FIG. 1 has, for example, an upper section 2 having a multi-tray distillation column structure or a packed column structure, and a lower section 3 having a packed column structure, and the upper section 2 and the lower section 3 are connected to each other optionally through a connective section having a certain length, to form a reactor.

In the distillation column reactor usable for the process of the present invention as shown in FIG. 1, the lower section 3 of the reactor 1 as shown in FIG. 1 has an upper portion 3b and a bottom portion 4. Through the upper portion 3b, the circulating liquid fraction and the alkyl alcohol liquid feed flows downward to the bottom portion 4 in which the liquid bottom faction is accumulated.

As shown in FIG. 1, preferably a feed gas-feeding conduit 5 for feeding a feed gas containing nitrogen oxide is connected to a lower end portion of the upper portion 3b, and an alkyl alcohol-feed conduit 6 for feeding an alkyl alcohol liquid is connected to an upper portion of the upper section 2 of the reactor 1.

In the distillation column reactor usable for the present invention, as shown in FIG. 1, preferably a liquid fraction-circulating path 9a is formed from a conduit 4b for withdrawing the liquid bottom fraction from the bottom portion 4, a liquid-transporting means 7 (for example, a liquid-transporting pump), a conduit 4c, a cooler 8, a conduit 9 through which the cooled liquid fraction is returned into a portion immediately above the lower section 3, and the lower section 3 including the upper portion 3b and a bottom portion 4. Also, a discharge conduit 10 may be connected to the conduit 4c at a location immediately downstream from the liquid-transporting means 7.

Also, as shown in FIG. 1, to collect a gas fraction generated in the reactor 1 and containing the target alkyl nitrite from the top portion 11 of the reactor 1, a conduit 12 for delivering the target alkyl nitrite-containing gas fraction is connected to the top portion 11 of the reactor 1. Optionally, a discharge conduit 13 for discharging (purging) a portion of the gas fraction from the conduit 12 is connected to the conduit 12. The discharged portion of the gas fraction through the conduit 13 may be cooled by a cooler (not shown in FIG. 1), a resultant condensed substance is removed from the discharged gas fraction, and the remaining portion of the gas fraction comprising mainly an inert gas is discharged to the air atmosphere.

In the process of the present invention, the nitrogen oxide-containing feed gas for the distillation column reactor is preferably supplied from a process for producing an alkyl oxalate. In the alkyl oxalate-producing process, carbon monoxide and an alkyl nitrite are reacted with each other in the presence of a catalyst in a reactor, to produce a gas fraction containing a dialkyl oxalate; the resultant gas fraction is fed into an absorption column in which the gas fraction is brought into contact with an absorption liquid comprising an alkyl alcohol, to prepare a condensed liquid fraction containing the dialkyl oxalate absorbed in the alkyl alcohol-containing absorption liquid and a non-condensed gas fraction containing a vapor of the alkyl alcohol and gaseous nitrogen monoxide; and the non-condensed gas fraction is delivered from the absorption column and is fed, as a feed gas, into the distillation column reactor to produce the gas fraction containing the alkyl nitrite.

Figure 2:
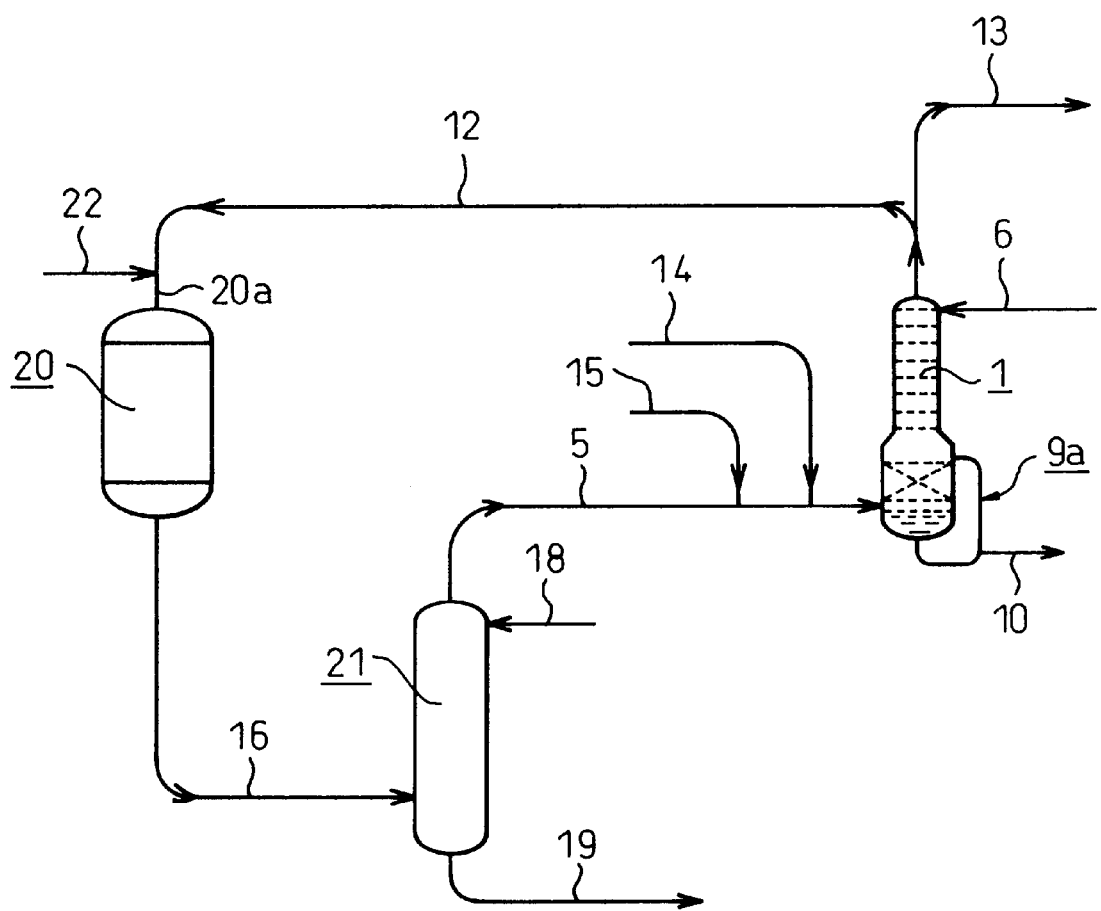
FIG. 2 is an explanatory diagram showing an embodiment of procedure for producing an oxalate diester from an alkyl nitrite produced by the process of the present invention.

In FIG. 2, carbon monoxide (CO) supplied through a conduit 22 and the gas fraction produced in the distillation column reactor 1, containing an alkyl nitrite and supplied through a conduit 12 are fed into a main reactor 20 through a conduit 20a containing a platinum group metal-containing catalyst. In the reactor 20, the carbon monoxide and the alkyl nitrite react with each other to prepare a dialkyl oxalate. The resultant gas fraction containing the dialkyl oxalate is withdrawn from the main reactor 20 and fed into a lower portion of a absorption column 21 through a conduit 16. A liquid absorber comprising an alkyl alcohol is fed into a top portion of the absorption column 21 through a conduit 18 and flows downward through the absorption column 21. The fed gas fraction flows upward through the absorption column 21 and comes into countercurrent contact with the flowing alkyl alcohol, to condense the dialkyl oxalate and dissolve in the alkyl alcohol. The resultant liquid fraction comprising the solution of the dialkyl oxalate in the alkyl alcohol is delivered and collected from the bottom of the absorption column 21 through a conduit 19. The collected liquid fraction is subjected to a distillation refining procedure to collect the dialkyl oxalate.

In FIG. 2, a non-condensed gas fraction generated in the absorption column 21 and comprising nitrogen monoxide as a major component, and carbon dioxide gas, nitrogen gas and alkyl alcohol vapor as minor components is withdrawn from the top portion of the absorption column 21 through a conduit 5.

The withdrawn gas fraction is used as a feed gas for the alkyl nitrite-producing reaction in the distillation column reactor 1.

The feed gas is optionally mixed with a molecular oxygen gas supplied through a conduit 14 and with an alkyl alcohol vapor supplied through a conduit 15, and fed into a lower section of the distillation column reactor 1 to subject it to the alkyl nitrite production process as mentioned above.

The process as shown in FIG. 2 can be utilized to produce a carbonate diester by using a specific catalyst in the main reactor 20, or to produce diesters by adding, as starting components, olefins.

As mentioned above, the process of the present invention can be utilized as an alkyl nitrite-regenerating procedure in the production process for dialkyl oxalate, for example, dimethyl oxalate or diethyl oxalate.

The dialkyl oxalate-production process comprises the steps of feeding carbon monoxide and an alkyl nitrite into a main reactor containing a catalyst, to produce a dialkyl oxalate by a catalytical reaction of the carbon monoxide with the alkyl nitrite;

introducing a gas fraction generated in the main reactor into an absorption column, to bring the gas fraction into contact with an absorbing liquid comprising an alkyl alcohol and to generate a condensed liquid fraction containing the dialkyl oxalate; introducing the condensed liquid fraction from the absorption column into a distillation refining procedure to collect the target dialkyl oxalate; withdrawing a non-condensed gas fraction generated in the absorption column and containing nitrogen monoxide and the alkyl alcohol vapor from a top portion of the absorption column; introducing the non-condensed gas fraction, as a feed gas, into a lower section of a distillation column reactor, while feeding an alkyl alcohol liquid into an upper section of the distillation column reactor, while allowing the fed alkyl alcohol liquid to flow downward through the distillation column reactor, and while withdrawing a portion of a liquid bottom fraction generated in the distillation column reactor and accumulated in a bottom portion of the distillation column reactor, cooling the withdrawn liquid fraction, and returning the cooled liquid fraction into a lower section of the distillation column reactor to allow the liquid fraction through the lower section of the distillation column reactor and to regenerate the alkyl nitrite by the reaction of the alkyl alcohol with the nitrogen oxide; and feeding a gas fraction generated in the distillation column reactor and containing the alkyl nitrite into the main reactor, in which distillation column reactor, (a) the total amount of the liquid fraction circulating through the lower section of the distillation column reactor is controlled to a level of 50 to 200 times the total amount of the alkyl alcohol fed into the distillation column reactor, (b) a molar ratio of the total molar amount of the alkyl alcohol fed into the distillation column reactor and the alkyl alcohol contained in the liquid fraction circulating through the lower section of the distillation column reactor to the molar amount of nitrogen oxide contained in the feed gas fed into the lower section of the distillation column reactor is controlled to 20:1 to 150:1, and (c) the content of the alkyl alcohol in the liquid bottom fraction accumulated in the bottom portion of the distillation column reactor is maintained at a level of 15 to 60% by weight.

In the process, the distillation column reactor serves as a regeneration reactor for an alkyl nitrite.

In the dialkyl oxalate production process, the circulation of the liquid fraction in the distillation column reactor is preferably carried out by withdrawing the liquid bottom fraction from the bottom portion of the reactor by a liquid transporting means, cooling the withdrawn liquid fraction, returning the cooled liquid fraction into an upper portion of the lower section whereby the returned liquid fraction flows downward through the lower section of the distillation column reactor.

In the circulation of the liquid fraction in the dialkyl oxalate production process, the withdrawn liquid fraction is preferably cooled to a temperature in the range of from 0° C. to 60° C. and of 1 to 30° C. below the original temperature of the withdrawn liquid fraction, and then the cooled liquid fraction is returned into the lower section of the distillation column reactor.

In the circulation of the liquid fraction in the dialkyl oxalate production process, a portion of the withdrawn liquid fraction may be discharged from the circulation path, and the remaining portion of the withdrawn liquid fraction may be cooled and then returned into the lower section of the distillation column reactor.

In the dialkyl oxalate production process, the reaction of the nitrogen oxide with the alkyl alcohol in the distillation column reactor is preferably carried out at a temperature of 0 to 100° C.

In the dialkyl oxalate production process, the total amount of the liquid fraction circulating through the lower section of the distillation column reactor is controlled to a level of 70 to 160 times the total amount of the alkyl alcohol fed into the distillation column reactor.

In the dialkyl oxalate production process, the feed gas introduced into the distillation column reactor contains nitrogen oxide in which the content of nitrogen monoxide is 50 molar % or more based on the total molar amount of the nitrogen oxide, and is added with molecular oxygen in an amount of 0.02 to 0.25 mole per mole of the nitrogen oxide.

In the dialkyl oxalate production process, the alkyl alcohol liquid is cooled to a temperature between −15° C. and 30° C., and the cooled alkyl alcohol liquid is fed into a top portion of the upper section of the distillation column reactor and flows downward from the upper section to the lower section of the distillation column reactor.

In the production of the dialkyl oxalate, the reaction of carbon monoxide with an alkyl nitrite is carried out in accordance with the following reaction formula (1):

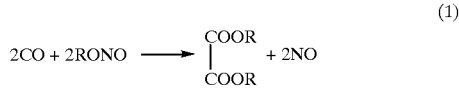

and the regeneration of an alkyl nitrite is effected in accordance with the following reaction formula (2):

The alkyl nitrite for the production of the dialkyl oxalate is preferably selected from those having 1 to 8 carbon atoms, more preferably 1 to 6 carbon atoms, still more preferably 1 to 2 carbon atoms, for example, methyl nitrite and ethyl nitrite.

The solid catalyst usable for the dialkyl oxalate producing reaction comprises a catalytic component selected from platinum group metals, for example, palladium, platinum, iridium, ruthenium and rhodium metals, and carried on a carrier formed from activated carbon, silicone carbide, magnesia, silica, zeolites, silica/alumina, and/or alumina (including γ-alumina and α-alumina).

There is no limitation to the method of preparing the solid catalyst. For example, the catalyst may be prepared by impregnating a carrier with an aqueous solution of a platinum group metal compound, reducing the platinum group metal compound carried on the carrier with a reducing agent, and drying and/or calcining the reduced metal-carrying carrier.

In another method of preparing the catalyst, the same impregnating and drying and/or calcining procedures as mentioned above are carried out, except that the reducing procedure is omitted; the resultant catalyst precursor is packed in a container, a reducing gas, for example, a hydrogen or carbon monoxide gas is introduced into the packed layer of the catalyst precursor at a temperature of 50 to 500° C., to reduce the platinum group compound into an elemental metal.

The platinum group metal compound usable for the catalyst is preferably selected from halogenated platinum group metal compounds, for example, palladium chloride, palladium bromide, platinum chloride and rhodium chloride, nitrate salt of the platinum group metals, for example, palladium nitrate and platinum nitrate, platinum group metal phosphate salts, for example, palladium phosphate, ruthenium phosphate, platinum group metal carboxylate salts, for example, palladium acetate and rhodium acetate. In the production of the alkyl nitrite, the catalytic metal is preferably selected from palladium chloride and palladium acetate.

The carrier for the catalyst preferably has a specific surface area of 0.01 to 200 $m^2/g$, particularly 0.05 to 100 $m^2/g$, more preferably 0.1 to 50 $m^2/g$, and an average pore size of 10 to 1,000 nm, particularly 50 to 500 nm, more preferably 100 to 300 nm. Also, the carrier preferably has a pore volume of 0.05 ml/g or more, particularly 0.1 to 3.0 ml/g, more preferably 0.3 to 0.6 ml/g. These values are measured by the BET method and the mercury-penetration method.

The above-mentioned carrier may be in the form of shaped articles, for example, pellets, or of grains or of fine particles. In the production of the alkyl oxalate, the carrier is preferably in the form of shaped articles, particularly compress-shaped articles such as pellets, having a size of 0.5 to 10 mm, or of grains having a 4 to 200 mesh size, or of fine particles having a particle size of 20 to 200 $\mu$m.

In the gas phase catalytic reaction of carbon monoxide with an alkyl nitrite, a feed gas comprising the alkyl nitrite, carbon monoxide and an inert gas such as nitrogen gas is fed into a main reactor packed with the catalyst. In this reaction, preferably the reaction temperature is 50 to 200° C., more preferably 80 to 150° C.; the reaction pressure is from the ambient atmospheric pressure to 20 $kg/cm^2G$, more preferably, from the ambient atmospheric pressure to 10 $kg/cm^2G$; the feed gas contact time is 0.1 to 20 seconds, more preferably 0.2 to 10 seconds; the content of the alkyl nitrite in the feed gas is 1 to 35% by volume, more preferably 3 to 30% by volume; and the content of carbon monoxide in the feed gas is 1 to 90% by volume, more preferably 5 to 60% by volume.

The main reactor may be selected from fixed bed, fluidized bed, and moving bed reactors. From the view-point of industry, the fixed bed reactor is preferred.

In the absorption step of the dialkyl oxalate production process, the gas fraction produced in the main reaction step and containing the dialkyl oxalate is withdrawn from the main reactor 20 through the conduit 16 and introduced into a bottom portion of an absorption column 21, while feeding an alkyl alcohol liquid (absorption liquid) into a top portion of the absorption column 21 through a conduit 18, whereby the gas fraction flowing upward comes into contact with the alkyl alcohol liquid flowing downward in the absorption column 21, the dialkyl oxalate in the gas fraction is condensed and dissolved in the alkyl alcohol liquid, and the resultant dialkyl oxalate solution is withdrawn from the bottom portion of the absorption column 21 through a conduit 19. Also, a non-condensed gas fraction containing nitrogen monoxide is withdrawn from the top portion of the absorption column 21 and fed into a lower section of the distillation column reactor (an alkyl nitrate-regeneration reactor) 1 through a conduit 5.

The inside temperature of the absorption column is preferably −30 to 80° C., more preferably −20 to 60° C. The alkyl alcohol for the absorption liquid is preferably selected from alkyl alcohols having 1 to 6 carbon atoms, for example, methyl alcohol, ethyl alcohol, n-propyl alcohol, isopropyl alcohol, n-butyl alcohol and isobutyl alcohol.

The absorption liquid is preferably fed in an amount of 1 to 100 parts by weight, more preferably 2 to 20 parts by weight, per 100 parts by weight of the dialkyl oxalate produced in the main reactor 20 and fed into the absorption column 21. The absorption liquid preferably has a temperature of −20 to 20° C. when introduced into the absorption column.

The absorption column may be selected from multi-tray absorption columns, for example, sieve tray columns, bubble bell columns and valve tray columns, and packed columns packed with packing materials, for example, Poll rings and Raschig rings.

The regeneration of the alkyl nitrite by the distillation column reactor 1 can be carried out by the procedures as mentioned above.

The gas fraction generated in the distillation column reactor 1 and containing the alkyl nitrite is withdrawn from the top portion of the distillation column reactor 1 through a conduit 12 and fed into the main reactor 20 through a conduit 20a. A portion of the withdrawn gas fraction is optionally discharged to the outside of the system through a conduit 13.

EXAMPLES

The present invention will be further illustrated by the following examples.

Example 1

A distillation column reactor 1 as shown in FIG. 1 was employed. This reactor 1 was of a packed column type reactor having an inside diameter of 158 mm and a height of 1400 mm and included a 10 mm Raschig ring-packed upper layer (an upper section 2) having a length of 800 mm from a level of 50 mm below the column top and a 10 mm Raschig ring-packed lower layer (a lower section 3) having a length of 400 mm from a level of 30 mm below the bottom of the upper layer.

A feed gas containing 15% by volume of nitrogen monoxide and 85% by volume of nitrogen was fed into a lower portion of the lower section 3 of the reactor 1 through a conduit 5, at a feed rate of 15.0 $Nm^3$/hr under a pressure of 2.2 kg/cm2G, and simultaneously oxygen gas was fed into the above-mentioned lower portion through a conduit 14 at a feed rate of 0.5 $Nm^3$/hr.

Also, a methyl alcohol liquid having a temperature of 20° C. was fed into a top portion of the upper section 2 of the distillation column reactor 1 through a supply conduit 6 at a feed rate of 5.7 liters/hr. The inside pressure of the distillation column reactor 1 was controlled so that the pressure of the top portion of the upper section 2 became 2.0 kg/cm2G.

A liquid bottom fraction accumulated in the bottom portion 4 of the reactor 1 was withdrawn through a conduit 4b, forwarded to a cooler (a heat exchanger type cooler) 8 through a pump 7 and conduit 4c and returned into a portion located immediately above the lower section 3 at a flow rate of 360 liters/hr.

The circulating amount (weight) of the liquid fraction was controlled to 73 times by weight the total amount (weight) of methyl alcohol fed into the reactor 1, and the withdrawn liquid fraction was cooled by passing cold water having a temperature of 5° C. through a cooling jacket of the cooler 8, so that the temperature of the liquid bottom fraction accumulated in the bottom portion of the lower section 3 becomes 40° C.

The total amount of the methyl alcohol fed into the reactor and the methyl alcohol contained in the circulating liquid fraction is 41.9 moles per mole of nitrogen monoxide fed into the reactor 1.

After the operation in the reactor 1 became stable, the compositions of the resultant liquid fraction and gas fraction were measured. In the measurement results, a gas fraction was delivered at a delivery rate of 15.67 $Nm^3$/hr from the top portion of the reactor 1 through a conduit 12, and contained 12.4% by volume of methyl nitrite, 1.6% by volume of nitrogen monoxide, 4.7% by volume of methyl alcohol, 81.4% by weight of nitrogen. Also, the gas fraction had a water content of 0.05% by volume or less.

The liquid bottom fraction in the bottom portion of the reactor 1 contained 40.1% by weight of methyl alcohol, 52.2% by weight of water, 7.4% by weight of nitric acid and 0.4% by weight of methyl nitrite. A portion of the withdrawn liquid fraction was discharged at a discharge rate of 1.66 liters/hr through the conduit 10 arranged downstream from the outlet of the pump 7.

In the above-mentioned methyl nitrite-producing procedure of Example 1, nitric acid was produced, as a by-product, in an amount of 0.018 mole per mole of nitrogen monoxide fed into the reactor 1. The amount of nitric acid corresponded to 2.0% by mole based on the molar amount of nitrogen monoxide consumed in the reaction in the distillation column reactor 1.

Example 2

The same methyl nitrite-producing procedures as in Example 1 were carried out with the following exceptions.

A feed gas comprising 15.2% by volume of carbon monoxide, 4.8% by volume of methyl nitrite, 9.9% by volume of nitrogen monoxide, 6.8% by volume of methyl alcohol, 1.7% by volume of carbon dioxide and 61.6% by volume of nitrogen was fed at a feed rate of 15.0 $Nm^3$/hr under a pressure of 3.1 $kg/cm^3$G into the lower section of the reactor 1.

Simultaneously an oxygen gas was mixed at a feed rate of 0.15 $Nm^3$/hr into the feed gas. The mixed feed gas was introduced into a lower portion of the lower section 3 of the reactor 1. Also, a methyl alcohol liquid having a temperature of 20° C. was fed at a feed rate of 1.44 liters/hr into the top portion of the reactor 1 through a conduit 6. Further, the inside pressure of the reactor 1 was controlled to such an extent that the pressure in the top portion of the reactor 1 became 2.9 $kg/cm^2$G.

In the same manner as in Example 1, the liquid bottom fraction in the bottom portion of the reactor 1 was withdrawn through the conduit 4b by a pump 7, cooled by the cooler 8 and returned at a flow rate of 360 liters/hr into a portion immediately above the lower section 3 of the reactor 1. In the cooler 8, cooling water having a temperature of 5° C. was circulated through a cooling jacket of the cooler 8, to control the temperature of the liquid bottom fraction in the bottom portion of the reactor 1 to 40° C.

The amount of the circulating liquid fraction was 154 times the total amount of the methyl alcohol fed into the reactor 1. Also the molar ratio of the total molar amount of the methyl alcohol fed into the reactor 1 and the methyl alcohol contained in the circulating liquid fraction to the molar amount of nitrogen monoxide fed into the reactor 1 was 97.1:1.

After the reaction operation in the reactor 1 is stabilized, the same measurements as in Example 1 were carried out. In the measurement results, the gas fraction generated in the reactor 1 and having a water content of 0.05% by volume or less delivered at a delivery rate of 15.0 $Nm^3$/hr from the top portion of the reactor 1 through the conduit 12, contained 15.2% by volume of carbon monoxide, 8.7% by volume of methyl nitrite, 5.9% by volume of nitrogen monoxide, 6.8% by volume of methyl alcohol, 1.7% by volume of carbon dioxide and 61.7% by volume of nitrogen.

The liquid fraction generated in the reactor 1 contained 51.1% by weight of methyl alcohol, 41.5% by weight of water, 7.0% by weight of nitric acid, and 0.4% by weight of methyl nitrite, and a portion of the liquid fraction was discharged at a discharge rate of 0.63 liter/hr through the conduit 10 arranged downstream from the outlet of the pump 7.

In Example 2, the amount of nitric acid produced in the reactor 1 was 0.010 mole per mole of nitrogen monoxide fed into the reactor 1. Also, the amount of nitric acid produced in the reactor 1 was 2.5 molar % based on the molar amount of nitrogen monoxide consumed by the reaction occurred in the reactor 1.

Example 3

A synthesis of methyl nitrite was carried out by the same procedures as in Example 2 with the following exceptions.

The feeding of the methyl alcohol liquid having a temperature of 20° C. into the top portion of the reactor 1 through the conduit 6 was carried out at a feed rate of 2.70 liters/hr. The oxygen gas was fed at a feed rate of 0.34 $Nm/^3hr$. The amount of the circulating liquid fraction was 95 times by weight the total amount of methyl alcohol fed into the reactor 1. Also the total molar amount of the methyl alcohol fed into the reactor 1 and the methyl alcohol contained in the circulating liquid fraction was 38.4 moles per mole of nitrogen monoxide fed into the reactor 1.

The same measurements as in Example 1 were effected.

The gas fraction generated in the reactor and having a water content of 0.05% by volume or less was delivered at a delivery rate of 14.98 $Nm^3$/hr from the top portion of the reactor 1 through the conduit 12.

The gas fraction contained 15.2% by volume of carbon monoxide, 13.8% by volume of methyl nitrite, 0.8% by volume of nitrogen monoxide, 6.8% by volume of methyl alcohol, 1.7% by volume of carbon dioxide and 61.7% by volume of nitrogen.

The liquid fraction generated in the reactor 1 contained 22.6% by weight of methyl alcohol, 69.7% by weight of water, 7.5% by weight of nitric acid and 0.2% by weight of methyl nitrite. A portion of the liquid fraction was discharged at a discharge rate of 0.87 liter/hr through a conduit 10 arranged downstream from the outlet of the pump 7.

In Example 3, the amount of nitric acid produced in the reactor 1 was 0.014 mole per mole of nitrogen monoxide fed into the reactor 1. Also, the amount of nitric acid produced in the reactor 1 was 1.5 molar % based on the amount of nitrogen monoxide consumed by the reaction occurred in the reactor 1.

Comparative Example 1

A synthesis of methyl nitrite was carried out by the same procedures as in Example 3 except that the circulation of the liquid fraction was stopped during the reaction.

The break of the liquid fraction circulation caused the temperature in the lower section 3 of the reactor 1 to rapidly rise and thus the reaction not to be stably continued. Therefore, the feed of the materials was stopped.

Comparative Example 2

A synthesis of methyl nitrite was carried out by the same procedures as in Example 2, except that the methyl alcohol liquid with a temperature of 20° C. was fed at a feed rate of 2.50 liters/hr into the top portion of the reactor 1 through the conduit 6.

The amount of the circulating liquid fraction was 137 times by weight the total amount of the methyl alcohol fed into the reactor 1. Also the molar ratio of the total molar amount of the methyl alcohol fed into the reactor 1 and the methyl alcohol contained in the circulating liquid fraction to the molar amount of nitrogen monoxide fed into the reactor 1 was 175.3:1.

After the reaction operation in the reactor 1 is stabilized, the same measurements as in Example 1 were carried out. In the measurement results, the gas fraction generated in the reactor 1 and having a water content of 0.05% by volume or less delivered at a delivery rate of 14.98 $Nm^3$/hr from the top portion of the reactor 1 through the conduit 12, and contained 15.3% by volume of carbon monoxide, 8.6% by volume of methyl nitrite, 5.9% by volume of nitrogen monoxide, 6.7% by volume of methyl alcohol, 1.7% by volume of carbon dioxide and 61.8% by volume of nitrogen.

The liquid fraction generated in the reactor 1 contained 78.1% by weight of methyl alcohol, 16.0% by weight of water, 5.3% by weight of nitric acid, and 0.6% by weight of methyl nitrite, and a portion of the liquid fraction was discharged at a discharge rate of 1.60 liter/hr through the conduit 10 arranged downstream from the outlet of the pump 7.

In Comparative Example 2, the amount of nitric acid produced in the reactor 1 was 0.018 mole per mole of nitrogen monoxide fed into the reactor 1. Also, the amount of nitric acid produced in the reactor 1 was 4.5 molar % based on the molar amount of nitrogen monoxide consumed by the reaction occurred in the reactor 1.

Comparative Example 3

A synthesis of methyl nitrite was carried out by the same procedures as in Example 3, except that the methyl alcohol liquid with a temperature of 20° C. was fed at a feed rate of 2.46 liters/hr into the top portion of the reactor 1 through the conduit 6.

The weight of the circulating liquid fraction was 110 times the total weight of the methyl alcohol fed into the reactor 1. Also the molar ratio of the total molar amount of the methyl alcohol fed into the reactor 1 and the methyl alcohol contained in the circulating liquid fraction to the molar amount of nitrogen monoxide fed into the reactor 1 was 20.1:1.

After the reaction operation in the reactor 1 is stabilized, the same measurement as in Example 1 were carried out. In the measurement results, the gas fraction generated in the reactor 1 and having a water content of 0.05% by volume or less delivered at a delivery rate of 14.90 $Nm^3$/hr from the top portion of the reactor 1 through the conduit 12, and contained 15.3% by volume of carbon monoxide, 13.4% by volume of methyl nitrite, 0.7% by volume of nitrogen monoxide, 6.8% by volume of methyl alcohol, 1.7% by volume of carbon dioxide and 62.1% by volume of nitrogen.

The liquid fraction generated in the reactor 1 contained 10.0% by weight of methyl alcohol, 59.7% by weight of water, 30.3% by weight of nitric acid, and 0.2% by weight of methyl nitrite, and a portion of the liquid fraction was discharged at a discharge rate of 1.03 liter/hr through the conduit 10 arranged downstream from the outlet of the pump 7.

In Comparative Example 3, the amount of nitric acid produced in the reactor 1 was 0.067 mole per mole of nitrogen monoxide fed into the reactor 1. Also, the amount of nitric acid produced in the reactor 1 was 7.2 molar % based on the molar amount of nitrogen monoxide consumed by the reaction occurred in the reactor 1.

Comparative Example 4

A synthesis of methyl nitrite was carried out by the same procedures as in Example 2, except that the flow rate of the circulating liquid fraction was changed from 360 liters/hr to 120 liters/hr.

The weight of the circulating liquid fraction was 35 times the total weight of the methyl alcohol fed into the reactor 1. Also, the molar ratio of the total molar amount of methyl alcohol fed into the reactor 1 and methyl alcohol contained in the circulating liquid fraction to the molar amount of nitrogen monoxide fed into the reaction 1 was 16.5:1.

The same measurements as in Example 1 were effected.

The gas fraction generated in the reactor and having a water content of 0.05% by volume or less was delivered at a delivery rate of 14.93 $Nm^3$/hr from the top portion of the reactor 1 through the conduit 12.

The gas fraction contained 15.3% by volume of carbon monoxide, 13.6% by volume of methyl nitrite, 0.7% by volume of nitrogen monoxide, 6.8% by volume of methyl alcohol, 1.7% by volume of carbon dioxide and 61.9% by volume of nitrogen.

The liquid fraction generated in the reactor 1 contained 24.5% by weight of methyl alcohol, 55.7% by weight of water, 19.8% by weight of nitric acid and 0.2% by weight of methyl nitrite. A portion of the liquid fraction was discharged at a discharge rate of 1.07 liter/hr through a conduit 10 arranged downstream from the outlet of the pump 7.

In Comparative Example 4, the amount of nitric acid produced in the reactor 1 was 0.045 mole per mole of nitrogen monoxide fed into the reactor 1. Also, the amount of nitric acid produced in the reactor 1 was 4.9 molar % based on the amount of nitrogen monoxide consumed by the reaction occurred in the reactor 1.

In the process of the present invention in which the liquid bottom fraction accumulated in a bottom portion of a distillation column reactor and containing 10 to 60% by weight of an alkyl alcohol was withdrawn from the bottom portion, cooled by a cooler, and returned to a portion immediately above the lower section of the reactor, to circulate the liquid fraction through the lower section of the reactor under the specific conditions (a), (b) and (c) mentioned above, the reaction heat vigorously generated by the gas/liquid contact reaction in the lower section of the reactor can be surely removed with a high efficiency, and the gas/liquid contact reaction can be effected in the reaction system under appropriate conditions at a high degree of stability to produce an alkyl nitrite and, simultaneously, the production of nitric acid as a by-product can be restricted to a low level.

Example 4

A methyl nitrite-containing gas fraction was prepared from a feed gas comprising a gas fraction delivered from the following process for producing a dialkyl oxalate.

First Step

Alumina catalyst pellets having a diameter of 5 mm and a length of 3 mm and each carrying thereon 0.5% by weight of palladium were packed in an amount of 3.3 liters in 6 stainless steel tubes forming a multi-tube type reactor and each having a inside diameter of 36.7 mm and a height of 550 mm.

A mixed gas was prepared by mixing a carbon monoxide gas and a gas fraction supplied from a distillation column reactor which will be explained later.

The mixed gas comprised 18.6% by volume of carbon monoxide, 8.5% by volume of methyl nitrite, 5.7% by volume of nitrogen monoxide, 6.5% by volume of methyl alcohol, 1.5% by volume of carbon dioxide and 59.2% by volume of nitrogen and had a pressure of 3.5 kg/cm G.

The mixed gas was pre-heated to a temperature of about 90° C. by a heat exchanger and then fed into the top portions of the catalyst-packed tubes of the multi-tube type reactor through a gas compress-circulator at a feed rate of 15.6 $Nm^3$/hr, while circulating a hot water through heating jackets surrounding the shell of the reactor to maintain the temperature of the catalyst layers packed in the reactor tube at 105 to 120° C. In the reactor, carbon monoxide reacts with methyl nitrite to produce a dimethyl oxalate-containing gas fraction.

Second Step

A gas/liquid contact condenser type absorption column having an inside diameter of 158 mm and a height of 1400 mm and packed with Raschig rings was used.

The whole amount of the gas fraction produced by passing through the catalyst layers in the reactor was introduced into a bottom portion of the absorption column, while introducing an absorption liquid, namely a methyl alcohol liquid, at a feed rate of 0.15 liters/hr into a top portion of the absorption column, to bring the gas fraction and the methyl alcohol liquid into a countercurrent contact with each other. A condensed liquid fraction produced in the absorption column and containing 90.9% by weight of dimethyl oxalate, 2.0% by weight of dimethyl carbonate, 0.1% by weight of methyl formate, and 6.5% by weight of methyl alcohol was delivered from the bottom of the absorption column at a delivery rate of 1.74 kg/hr. Also, a non-condensed gas fraction generated in the absorption column and containing 15.2% by volume of carbon monoxide, 4.8% by volume of methyl nitrite, 9.9% by volume of nitrogen monoxide, 6.8% by volume of methyl alcohol, 1.7% by volume of carbon dioxide and 61.6% by volume of nitrogen was delivered at a delivery rate of 15.0 $Nm^3$/hr from the top of the absorption column.

Third Step

A packed column type reactor 1 having an inside diameter of 158 mm and a height of 1400 mm as shown in FIG. 1 was used as a distillation column reactor. The reactor 1 had an upper section 2 consisting of a 10 mm Raschig ring-packed layer located 50 mm below the top of the reactor and having a length of 800 mm and a lower section 3 consisting of a 10 mm Raschig ring-packed layer located 30 mm below the upper section and having a length of 400 mm. The lower reaction 3 of the reactor 1 was connected to the top portion of the absorption column 21 through a conduit 5 as shown in FIG. 2.

The non-condensed gas fraction delivered from the top portion of the absorption column 21 was fed into the lower section 3 of the reactor 1 through the conduit 5 at a feed rate of 15.0 $Nm^3$/hr under a pressure of 3.1 $kg/cm^2$G, while oxygen gas was introduced at a flow rate of 0.15 $Nm^3$/hr into the conduit 5 through a conduit 14 and nitrogen monoxide gas was introduced at a flow rate 0.015 $Nm/^3hr$ into the conduit 5 through a conduit 15, to mix the oxygen gas and the nitrogen monoxide gas into the non-condensed gas fraction and to provide a feed gas.

Simultaneously, a methyl alcohol liquid having a temperature of 20° C. was fed at a feed rate of 1.44 liters/hr into the top portion of the distillation column reactor 1 through a conduit 6. The inner pressure of the reactor 1 was controlled to such an extent that the pressure in the top portion of the reactor 1 is maintained at 2.9 kg/cm G. A resultant liquid bottom fraction accumulated in the bottom portion of the reactor 1 was circulated at a circulation rate of 360 liters/hr through a circulation path 9a including the conduit 4b, the pump 7, the conduit 4c, the cooler 8, the conduit 9 and the lower section 3 of the reactor 1 as shown in FIG. 1.

In the third step, the weight ratio of the amount of the circulating liquid fraction to the total amount of the methyl alcohol fed into the reactor 1 was controlled to 154:1. The temperature of the circulating liquid fraction was adjusted to 40° C. measured in the bottom portion of the reactor 1, by circulating a cooling water having a temperature of 5° C. through a cooling jacket of the cooler 8. Also, the molar ratio of the total molar amount of the methyl alcohol fed into the reactor 1 and methyl alcohol contained in the circulating liquid fraction to the molar amount of nitrogen monoxide fed to the reactor is controlled to 97.1:1.

The same measurements as in Example 1 were applied to the reaction results of the third step.

The gas fraction generated in the reactor 1 and having a water content of 0.05% by volume or less was delivered at a delivery rate of 15.0 $Nm^3$/hr from the top portion of the reactor 1 through the conduit 12.

The gas fraction contained 15.2% by volume of carbon monoxide, 8.9% by volume of methyl nitrite, 5.9% by volume of nitrogen monoxide, 6.8% by volume of methyl alcohol, 1.7% by volume of carbon dioxide and 61.7% by volume of nitrogen.

The liquid fraction generated in the reactor 1 contained 51.1% by weight of methyl alcohol, 41.5% by weight of water, 7.0% by weight of nitric acid. and 0.4% by weight of methyl nitrite. A portion of the liquid fraction was discharged at a discharge rate of 0.63 liter/hr through a conduit 10 arranged downstream from the outlet of the pump 7.

In the third step of Example 5, the amount of nitric acid produced in the reactor 1 was 0.010 mole per mole of nitrogen monoxide fed into the reactor 1. Also, the amount of nitric acid produced in the reactor 1 was 2.5 molar % based on the molar amount of nitrogen monoxide consumed by the reaction occurred in the reactor 1.

Fourth Step

The condensed liquid fraction delivered from the absorption column in the second step was introduced at a feed rate of 1.74 kg/hr into a distillation column (packed column, not shown in FIGS. 1 and 2) having an inside diameter of 50 mm and a height of 3 mm, and distilled under conditions of a column top temperature of 64.5° C. and a column bottom temperature of 166° C. A liquid fraction consisting essentially of dimethyl oxalate having a degree of purity of 99.8% by weight was delivered at a delivery rate of 1.57 kg/hr from the bottom of the distillation column. Also, a distillate fraction comprising 82.2% by weight of methyl alcohol, 17.7% by weight of dimethyl carbonate, and 0.1% by weight of methyl formate was delivered at a delivery rate of 0.17 liter/hr from the top of the distillation column.

Example 5

Methyl oxalate was prepared by the same procedure as in Example 4, with the following exceptions.

In the second step, the methyl alcohol liquid was fed at a feed rate of 0.34 liter/hr into the absorption column 21.

In the third step, the methyl alcohol liquid having a temperature of 20° C. was fed at a feed rate of 2.70 liters/hr into the top portion of the distillation column reactor 1 through the conduit 6.

The gas fraction delivered from the absorption column 21 of the second step was mixed with the oxygen gas introduced at a feed rate of 0.34 $Nm^3$/hr through the conduit 14 and the nitrogen monoxide gas introduced at a feed rate of 0.021 $Nm^3$/ hr through the conduit 15 to provide a feed gas for the third step.

The gas fraction delivered from the third step and supplied to the first step contained 18.6% by volume of carbon monoxide, 9.8% by volume of methyl nitrite, 4.2% by volume of nitrogen monoxide, 6.6% by volume of methyl alcohol and 59.3% by volume of nitrogen.

In the third step, the weight ratio of the amount of the circulating liquid fraction to the total amount of the methyl alcohol fed into the distillation column reactor 1 was 95:1. Also, the molar ratio of the total molar amount of methyl alcohol fed into the reactor 1 and methyl alcohol contained in the circulating liquid fraction to the molar amount of nitrogen monoxide fed into the reactor 1 was 38.4:1.

The same measurements as in Example 1 were applied to the reaction results of the third step.

The gas fraction generated in the distillation column reactor and having a water content of 0.05% by volume or less was delivered at a delivery rate of 14.98 $Nm^3$/hr from the top portion of the reactor 1 through the conduit 12.

The delivered gas fraction contained 10.9% by volume of carbon monoxide, 19.8% by volume of methyl nitrite, 4.6% by volume of nitrogen monoxide, 7.2% by volume of methyl alcohol, 1.6% by volume of carbon dioxide and 64.9% by volume of nitrogen.

The liquid fraction generated in the distillation column reactor 1 contained 22.6% by weight of methyl alcohol, 69.7% by weight of water, 7.5% by weight of nitric acid and 0.2% by weight of methyl nitrite. A portion of the liquid fraction was discharged at a discharge rate of 0.87 liter/hr through a conduit 10 arranged downstream from the outlet of the pump 7.

In Example 5, the amount of nitric acid produced in the reactor 1 was 0.014 mole per mole of nitrogen monoxide fed into the reactor 1. Also, the amount of nitric acid produced in the reactor 1 was 1.5 molar % based on the molar amount of nitrogen monoxide consumed by the reaction occurred in the reactor 1.

In the fourth step, dimethyl oxalate having a degree of purity of 99.8% by weight was delivered at a delivery rate of 3.47 kg/hr from the bottom portion of the distillation column. Also, a distillate fraction containing 82.0% by weight of methyl alcohol, 17.9% by weight of dimethyl carbonate and 0.1% by weight of methyl formate was delivered at a delivery rate of 0.39 liter/hr from the bottom portion of the distillation column.

Comparative Example 5

The same procedures for producing dimethyl oxalate as in Example 5 were carried out except that, in the third step using the distillation column reactor 1, the circulation of the liquid fraction was stopped during the reaction.

The break of the liquid fraction circulation caused the temperature in the lower section of the reactor 1 to rapidly increase and thus the reaction of the third step not to be stably continued. Therefore, the feed of the feed gas containing the non-condensed gas fraction, supplied from the absorption column of the second step, was stopped.

Comparative Example 6

Methyl oxalate was prepared by the same procedure as in Example 5, with the following exceptions.

In the third step, the methyl alcohol liquid having a temperature of 20° C. was fed at a feed rate of 2.50 liters/hr into the top portion of the distillation column reactor 1 through the conduit 6.

In the third step, the weight ratio of the amount of the circulating liquid fraction to the total amount of the methyl alcohol fed into the distillation column reactor 1 was 137:1. Also, the molar ratio of the total molar amount of methyl alcohol fed into the reactor 1 and methyl alcohol contained in the circulating liquid fraction to the molar amount of nitrogen monoxide fed into the reactor 1 was 175.3:1.

The same measurements as in Example 1 were applied to the reaction results of the third step.

The gas fraction generated in the distillation column reactor and having a water content of 0.05% by volume or less was delivered at a delivery rate of 14.24 Nm$^3$/hr from the top portion of the reactor 1 through the conduit 12.

The delivered gas fraction contained 10.9% by volume of carbon monoxide, 10.9% by volume of methyl nitrite, 4.6% by volume of nitrogen monoxide, 7.2% by volume of methyl alcohol, 1.6% by volume of carbon dioxide and 64.9% by volume of nitrogen.

The liquid fraction generated in the distillation column reactor 1contained 78.1% by weight of methyl alcohol, 16.0% by weight of water, 5.3% by weight of nitric acid and 0.6% by weight of methyl nitrite. A portion of the liquid fraction was discharged at a discharge rate of 1.60 liters/hr through a conduit 10 arranged downstream from the outlet of the pump 7.

In Comparative Example 6, the amount of nitric acid produced in the reactor 1 was 0.018 mole per mole of nitrogen monoxide fed into the reactor 1. Also, the amount of nitric acid produced in the reactor 1 was 4.5 molar % based on the amount of nitrogen monoxide consumed by the reaction occurred in the reactor 1. Thus, in the third step, nitrogen monoxide was fed at a feed rate of 0.030 Nm/$^3$hr, into the distillation column reactor 1.

In the fourth step, dimethyl oxalate having a degree of purity of 99.8% by weight was delivered at a delivery rate of 3.45 kg/hr from the bottom portion of the distillation column.

Comparative Example 7

Methyl oxalate was prepared by the same procedure as in Example 5, with the following exceptions.

In the third step, the methyl alcohol liquid having a temperature of 20° C. was fed at a feed rate of 2.48 liters/hr into the top portion of the distillation column reactor 1 through the conduit 6.

In the third step, the weight ratio of the amount of the circulating liquid fraction to the total amount of the methyl alcohol fed into the distillation column reactor 1 was 110:1. Also, the molar ratio of the total molar amount of methyl alcohol fed into the reactor 1 and methyl alcohol contained in the circulating liquid fraction to the molar amount of nitrogen monoxide fed into the reactor 1 was 20.1:1.

The same measurements as in Example 1 were applied to the reaction results of the third step.

The gas fraction generated in the distillation column reactor and having a water content of 0.05% by volume or less was delivered at a delivery rate of 14.90 Nm$^3$/hr from the top portion of the reactor 1 through the conduit 12.

The delivered gas fraction contained 10.9% by volume of carbon monoxide, 10.8% by volume of methyl nitrite, 4.6% by volume of nitrogen monoxide, 7.2% by volume of methyl alcohol, 1.6% by volume of carbon dioxide and 64.9% by volume of nitrogen.

The liquid fraction generated in the distillation column reactor 1 contained 10.0% by weight of methyl alcohol, 59.7% by weight of water, 30.3% by weight of nitric acid and 0.2% by weight of methyl nitrite. A portion of the liquid fraction was discharged at a discharge rate of 1.03 liters/hr through a conduit 10 arranged downstream from the outlet of the pump 7.

In Comparative Example 7, the amount of nitric acid produced in the reactor 1 was 0.067 mole per mole of nitrogen monoxide fed into the reactor 1. Also, the amount of nitric acid produced in the reactor 1 was 7.2 molar % based on the molar amount of nitrogen monoxide consumed by the reaction occurred in the reactor 1. Thus, in the third step, nitrogen monoxide was fed at a feed rate of 0.10 Nm/$^3$hr to the distillation column reactor 1.

In the fourth step, dimethyl oxalate having a degree of purity of 99.8% by weight was delivered at a delivery rate of 3.45 kg/hr from the bottom portion of the distillation column.

The process of the present invention for producing an alkyl nitrite is advantageously utilized as a step of a dimethyl oxalate production process, to regenerate an alkyl nitrite from a gas fraction separated from a reaction product of carbon monoxide with an alkyl nitrite and containing nitrogen monoxide.

In the regeneration step of the alkyl nitrite, the reaction heat generated in a lower section of a distillation column reactor can be removed by circulating the liquid fraction produced in the reactor through a circulating path including a pump, a cooler and the lower section of the reactor, with a high efficiency, and the target alkyl nitrite can be produced at a high yield, while restricting a side reaction producing nitric acid.

What we claim is:

1. A process for producing an alkyl nitrite comprising the steps of:
    (1) feeding an alkyl alcohol liquid cooled to a temperature of from −15° to 30 C. into a top portion of the upper section of a distillation column reactor in which the upper section is connected to a lower section having a bottom portion in which a liquid bottom fraction containing the alkyl alcohol is accumulated, while allowing the fed alkyl alcohol liquid to flow downward through the upper and lower sections of the distillation column reactor;
    (2) circulating the alkyl alcohol-containing liquid fraction through a circulating path through which the liquid bottom fraction is withdrawn from the bottom portion of the lower section of the distillation column reactor, the withdrawn liquid fraction is cooled to a temperature in the range from 0 to 50 C. and of 3 to 20 C. lower than the original temperature of the liquid bottom fraction in the bottom portion, and then the cooled liquid fraction is returned into an upper portion of the lower section of the distillation column reactor, thereby to cause the returned liquid fraction to flow downward through the lower section of the distillation column reactor;
    (3) introducing a feed gas containing nitrogen oxide into the lower section of the distillation column reactor, while allowing the fed feed gas to flow upward through the lower section of said distillation column reactor, and to come into countercurrent contact with the alkyl alcohol liquid and the alkyl alcohol-containing liquid fraction flowing downward through the lower section, whereby a gas-liquid reaction of the nitrogen oxide in the feed gas with the alkyl alcohol is effected at a temperature of 0 to 100 C. in the lower section to produce an alkyl nitrite; and
    (4) delivering a resultant gas fraction containing the alkyl nitrite from the distillation column reactor; wherein (a) the total amount of the liquid fraction circulating through the lower section of the distillation column reactor is controlled to a level of 50 to 200 times the total amount of the alkyl alcohol fed into of the distillation column reactor;

(b) the total molar amount of the alkyl alcohol fed into the distillation column reactor and the alkyl alcohol contained in the liquid fraction circulating through the lower section of the distillation column reactor is controlled in a molar ratio of 20:1 to 150:1 to the molar amount of nitrogen oxide contained in the feed gas fed into the lower section of the distillation column reactor; and (c) the content of the alkyl alcohol in the liquid bottom fraction accumulated in the bottom portion of the distillation column reactor is maintained at a level of 15 to 60% by weight.

2. The process for producing an alkyl nitrite as claimed in claim 1, wherein the circulating step is carried out by withdrawing the liquid bottom fraction from bottom portion of the lower section of the distillation column reactor through a conduit, cooling the withdrawn liquid fraction through a cooler, and returning the cooled liquid fraction into the upper portion of the lower section, whereby the returned liquid fraction flows downward through the lower section of the distillation column reactor.

3. The process for producing an alkyl nitrite as claimed in claim 1 wherein a portion of the liquid fraction withdrawn from the bottom portion of the lower section of the distillation column reactor is discharged from the circulating path and the remaining portion of the withdrawn liquid fraction is cooled and then returned into the upper portion of the lower section of the distillation column reactor.

4. The process for producing an alkyl nitrite as claimed in claim 1, wherein the total amount of the liquid fraction circulating through the lower section of the distillation column reactor is controlled to a level of 70 to 160 times the total amount of the alkyl alcohol fed into the distillation column reactor.

5. The process for producing an alkyl nitrite as claimed in claim 1, wherein the feed gas contains nitrogen monoxide in a content of 50 molar % or more based on the total molar amount of the nitrogen oxide presenting in the feed gas, and further contains molecular oxygen in an amount of 0.02 to 0.25 mole per mole of the nitrogen oxide.

6. The process for producing an alkyl nitrite as claimed in claim 1, wherein the feed gas for the distillation column reactor is supplied from a process for producing an alkyl oxalate in which carbon monoxide and an alkyl nitrite are reacted with each other in the presence of a catalyst in a reactor, to produce a gas fraction containing a dialkyl oxalate; the resultant gas fraction is fed into an absorption column in which the gas fraction is brought into contact with an absorption liquid comprising an alkyl alcohol, to prepare a condensed liquid fraction containing the dialkyl oxalate absorbed in the alkyl alcohol-containing absorption liquid and a non-condensed gas fraction containing a vapor of the alkyl alcohol and gaseous nitrogen monoxide; and the non-condensed gas fraction is delivered from the absorption column, and is fed, as a feed gas, into the distillation column reactor to produce the gas fraction containing the alkyl nitrite.

7. The process for producing an alkyl nitrite as claimed in claim 6, wherein the liquid fraction produced in the absorption column is fed into a distillation column refiner to collect the refined dialkyl oxalate.

8. The process for producing an alkyl nitrite as claimed in claim 6, wherein the gas fraction containing the alkyl nitrite is delivered from the distillation column reactor and supplied into the column reactor for producing the dialkyl oxalate-containing gas fraction.

9. The process for producing an alkyl nitrite as claimed in claim 1, wherein the alkyl alcohol is methyl alcohol and the alkyl nitrite is methyl nitrite.

* * * * *